(12) United States Patent
Sieracki et al.

(10) Patent No.: US 7,499,048 B2
(45) Date of Patent: Mar. 3, 2009

(54) BODY REGION INDICATION

(75) Inventors: Jeffrey M. Sieracki, Silver Spring, MD (US); Richard B. North, Baltimore, MD (US)

(73) Assignee: Medtronic, Inc., Minneapolis, MN (US)

( * ) Notice: Subject to any disclaimer, the term of this patent is extended or adjusted under 35 U.S.C. 154(b) by 478 days.

(21) Appl. No.: 10/696,491

(22) Filed: Oct. 29, 2003

(65) Prior Publication Data

US 2004/0136578 A1    Jul. 15, 2004

Related U.S. Application Data

(60) Provisional application No. 60/422,261, filed on Oct. 31, 2002, provisional application No. 60/503,215, filed on Sep. 15, 2003.

(51) Int. Cl.
*G06T 15/00* (2006.01)
(52) U.S. Cl. .................. 345/419; 345/156; 345/649; 700/17
(58) Field of Classification Search ......... 345/649–659, 345/156, 419; 700/17
See application file for complete search history.

(56) References Cited

U.S. PATENT DOCUMENTS

| | | | | |
|---|---|---|---|---|
| 5,563,625 A * | 10/1996 | Scott | ............................. | 345/658 |
| 5,588,098 A * | 12/1996 | Chen et al. | ................... | 345/653 |
| 5,615,318 A * | 3/1997 | Matsuura | ..................... | 345/420 |
| 5,778,882 A | 7/1998 | Raymond et al. | ............ | 600/513 |
| 5,938,690 A | 8/1999 | Law et al. | ....................... | 607/46 |
| 6,132,218 A | 10/2000 | Benja-Athon | ................ | 600/300 |
| 6,260,000 B1 * | 7/2001 | Karasaki et al. | .............. | 702/155 |
| 6,272,366 B1 | 8/2001 | Vining | .......................... | 600/407 |
| 6,281,872 B1 * | 8/2001 | Cariffe | ........................ | 345/658 |
| 6,308,102 B1 | 10/2001 | Sieracki et al. | ................ | 607/59 |
| 6,383,135 B1 | 5/2002 | Chikovani et al. | ............ | 600/300 |
| 6,609,032 B1 * | 8/2003 | Woods et al. | .................. | 607/46 |
| 6,654,027 B1 * | 11/2003 | Hernandez | ................... | 345/619 |

(Continued)

FOREIGN PATENT DOCUMENTS

WO    WO 01/93952    12/2001

OTHER PUBLICATIONS

Fowler, K.R., "Neurological Stimulation System", Proceedings AAMI 21st Annual Meeting, Apr. 12-16, p. 27, 1986.

(Continued)

*Primary Examiner*—Phu K Nguyen
(74) *Attorney, Agent, or Firm*—Shumaker & Sieffert, P.A.

(57) ABSTRACT

The invention is directed toward two-dimensional dynamic body image templates, and associated techniques, that allow a user to indicate regions of the human body. The body region indications may correspond to locations of injury, pain, treatment, discoloration, paresthesia, or the like. A user is presented with the body image templates and asked to indicate regions on the body templates that correspond to affected regions of a patient's body. The body image templates represent views of an external surface of a human body rotated about at least one axis. In exemplary embodiments, a user controls display of overlapping templates, which may allow the user to perceive rotation of a three-dimensional body surface. The user indicated regions from each of the displayed body image templates are stored in a body surface coordinate system, such that regions indicated via one template may be appropriately displayed on other templates.

60 Claims, 7 Drawing Sheets

U.S. PATENT DOCUMENTS

| | | | |
|---|---|---|---|
| 6,659,968 B1 | 12/2003 | McClure | 600/595 |
| 6,664,986 B1 * | 12/2003 | Kopelman et al. | 715/849 |
| 6,825,856 B1 * | 11/2004 | Fazzio et al. | 345/646 |
| 7,015,935 B2 * | 3/2006 | Herget et al. | 345/649 |
| 2003/0065589 A1 | 4/2003 | Giacchetti | 701/22 |
| 2003/0146942 A1 | 8/2003 | Helgason et al. | 345/771 |

OTHER PUBLICATIONS

Fowler, K. R., North, R.B.: "Patient-interactive PC interface to implanted, multichannel stimulators," Proceedings of 39th Annual Conference on Engineering in Medicine and Biology, p. 380, 1986.

North, R.B., Fowler, K.R., "Computer-controlled, patient-interactive, multichannel, implanted neurological stimulators," Applied Neurophysiology, 50:39-41, 1987.

North, R.B., Nigrin, D.J., Szymanski, R.E., Fowler, K.R., "Computer-controlled, multichannel, implanted neurological stimulation system: Clinical assessment," Pain (Suppl.), 5:S83, 1990.

Fowler, K.R., North, R.B., "Computer-optimized neurological stimulation," Proc. Ann. Internat. Conf. IEEE Engineering Medicine and Biology Soc., 13:1692-1693, 1991.

Fowler, K.R., North, R.B., "Computer-optimized neurostimulation," APL Technical Digest, 12:192-197, 1991.

North, R.B., et al., "Spinal cord stimulation for chronic intractable pain: superiority of 'multi-channel' devices," Pain, V44, pp. 119-130, 1991.

North, R.B., Fowler, K.R., "Computer-controlled, patient-interactive neurological stimulation system," (Abstract) Acta Neurochir, 117:90, 1992.

North, R.B., Fowler, K.R., Nigrin, D.A., Szymanski, R.E., "Patient interactive, computer-controlled neurological stimulation system: Clinical efficacy in spinal cord stimulator adjustment," Journal of Neurosurgery, 76:967-972, 1992.

North, R.B., Fowler, K.R., Nigrin, D.A., Szymanski, R.E., Piantadosi, S., "Automated 'pain drawing' analysis by computer-controlled, patient-interactive neurological stimulation system," Pain, 50:51-57, 1992.

North, R.B., "Spinal Cord Stimulation for Chronic Intractable Pain," Electrical and Magnetic Stimulation of the Brain and Spinal Cord, pp. 289-301, 1993.

North, R.B., "The Role of Spinal Cord Stimulation in Contemporary Pain Management," APS Journal, vol. 2, No. 2, pp. 91-99, 1993.

North, R. B., Kidd, D. H., Zahurak, M., James, C. S., Long, D. M., "Spinal cord stimulation for chronic, intractable pain: Experience over two decades," Neurosurgery, 32:384-395, 1993.

North, R.B., Fowler, K.R., "Patient-interactive, microprocessor-controlled neurological stimulation system" (abstract), Stereotactic and Functional Neurosurgery, 62:309-315, 1994.

North, R. B., Levy, R. M., "Consensus conference on the neurosurgical management of pain," Neurosurgery, 34:756-761, 1994.

North, R. B., Kidd, D. H., Lee, M. S., Piantadosi, S., "A prospective, randomized study of spinal cord stimulation versus reoperation for the failed back surgery syndrom," Stereotactic and Functional Neurosurgery, 62:267-272, 1994.

North, R.B., et al., "Spinal Cord Stimulation For Chronic Pain," Functional Neurosurgery, vol. 6, No. 1, pp. 145-155, Jan. 1995.

North, R.B., Cutchis, P., "Spinal cord stimulation for chronic intractable pain," Spinal Cord Stimulation II, pp. 49-63, Darmstadt, Steinkopff, 1995.

North, R.B., McNamee, P., Wu, L., Piantadosi,S., "Artificial neural networks: Application to electrical stimulation of the human nervous system," (abstract) Stereotactic and Functional Neurosurgery, 65:161, 1995.

North, R. B., Kidd, D. H., Wimberly, R. L., Edwin, D., "Prognostic value of psychological testing in spinal cord stimulation patients: A prospective study," Neurosurgery, 39:301-311, 1996.

North, R. B., Kidd, D. H., Zahurak, M., Piantadosi, S., "Specificity of diagnostic nerve blocks: A prospective, randomized study of sciatica due to lumbosacral spine disease," Pain, 65:77-85, 1996.

North, R.B., McNamee, P., Wu,L., Piantadosi, S., "Artificial neural networks: Application to electrical stimulation of the human nervous system," Neurosurgical Focus, 2(1:1):1-5, 1997.

Alo, K. M. et al., "Computer Assisted and Patient Interactive Programming of Dual Octrode Spinal Cord Stimulation in the Treatment of Chronic Pain," Neuromodulation, vol. 1, No. 1, pp. 30-45, 1998.

North, R.B., Sieracki, J.N., Fowler, K.R., Alvarez, B., Cutchis, P.N., "Patient-interactive, microprocessor-controlled neurological stimulation system," Neuromodulation, 1(4):185-193, 1998.

Khalessi, A. A., Taylor, R. S., Brigham, D. D., North, R. B., "Automated, patient-interactive spinal cord stimulator adjustment: A cost-minimization analysis," Neurosurgery, 53:501-502, 2003.

North, R. B., Calkins, S. K., Campbell, D. S., Sieracki, J. M., Piantadosi, S. A., Daly, M. J., Dey, P. B., Barolat, G., "Automated, patient-interactive spinal cord stimulator adjustment: A randomized, controlled trial," Neurosurgery 52:572-580, 2003.

U.S. Appl. No. 10/696,501, entitled "Implantable Neurostimulator Programming with Battery Longevity Indication", filed Oct. 29, 2003, Richard B. North, Kim R. Fowler, Jeffrey M. Sieracki, David D. Brigham.

U.S. Appl. No. 10/696,781, entitled "Neurostimulation Therapy Manipulation", filed Oct. 29, 2003, Richard B. North, Jeffrey M. Sieracki.

U.S. Appl. No. 10/696,725, entitled "Failsafe Programming of Implantable Medical Devices", filed Oct. 29, 2003, Richard B. North, Jeffrey M. Sieracki.

U.S. Appl. No. 10/696,494, entitled "Distributed System for Neurostimulation Therapy Programming", filed Oct. 29, 2003, Richard B. North, Kim R. Fowler, Jeffrey M. Sieracki.

U.S. Appl. No. 10/696,778, entitled "Applying Filter Information to Identify Combinations of Electrodes", filed Oct. 29, 2003, Richard B. North, Jeffrey M. Sieracki.

* cited by examiner

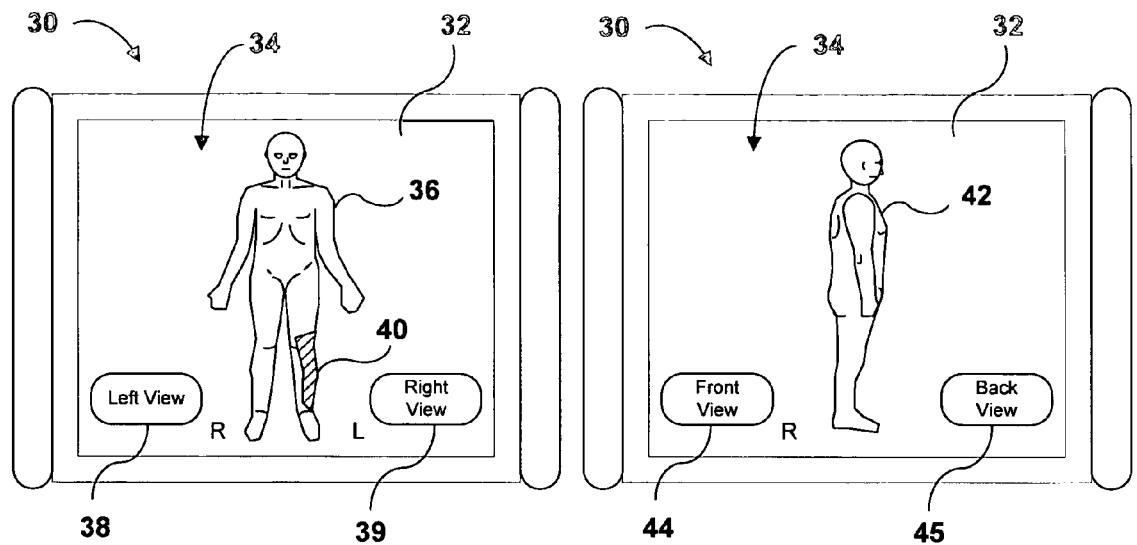
FIG. 2A  FIG. 2B
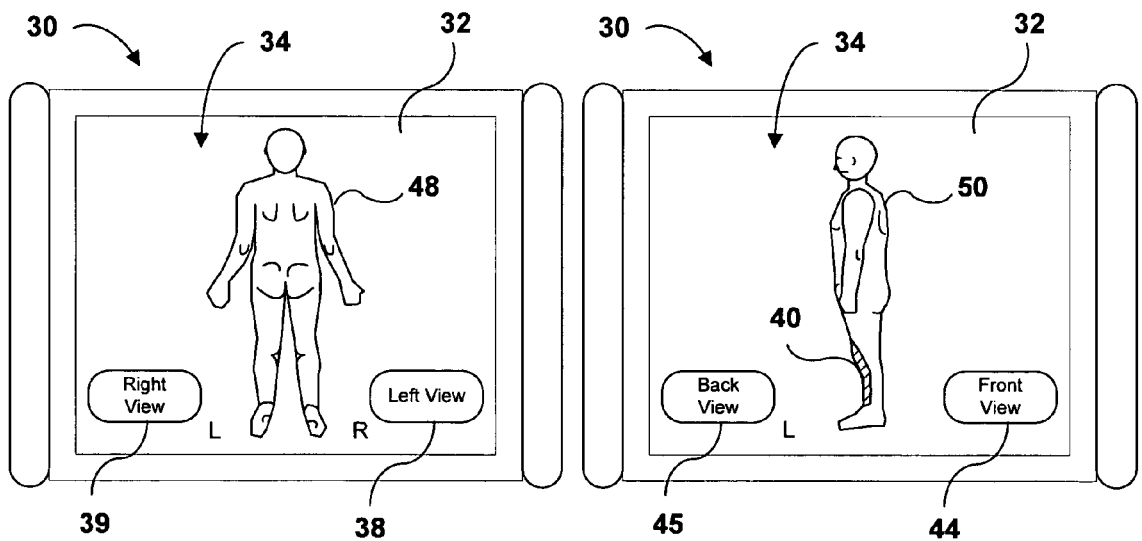
FIG. 2C  FIG. 2D

BODY REGION INDICATION

This application claims priority from U.S. Provisional Application Ser. No. 60/422,261, filed Oct. 31, 2002, and U.S. Provisional Application Ser. No. 60/503,215, filed Sep. 15, 2003. The entire content of both Provisional Applications is incorporated herein by reference.

TECHNICAL FIELD

The invention relates to medical devices, and to techniques for indicating regions of the body.

BACKGROUND

Body region indication systems are used to aid in diagnosis and treatment of patients by quantifying a patient's experience to a physician or a clinician. In particular, body region indication systems allow a user, such as a patient, nurse, clinician, or physician, to indicate points or regions of interest on the human body according to a uniform, standardized template. The indicated points or regions may include locations of injury, pain, treatment, discoloration, paresthesia, or the like.

Conventional body region indication systems have typically been based on two-dimensional drawing methods, e.g., allowing a user to draw on a printed outline or template of the human body. For example, a user may be presented with a blank body outline on a printout or a computer screen, and asked to circle or shade any affected areas. Such static, two-dimensional template systems are limited in that some areas of the body surface are not visible to the user. Hence the user must approximate the indication regions in invisible or partially visible areas by coloring near the edges of the template outlines. The approximations give inaccurate body indication results with respect to both the position and extent of the regions.

Some existing body region indication systems display both a front and back outline of the body. However, additional, mutually exclusive views always leave some areas of the body, e.g., the sides, difficult to indicate accurately because they are located at the edges of the body views. Further, users of such front and back body outline systems have difficulty associating the orientation of the patient with the orientation of the displayed templates. For example, leg pain may be indicated properly on the front outline of the body as the front of the left leg, but indicated incorrectly on the back outline of the body as the back of the right leg. The error is difficult to determine after entry, since the inaccurate indications may be medically reasonable.

Multiple, overlapping views could be used in an attempt to avoid the problems associated with having areas of the body not shown. Such templates, however, would require the user to either redundantly fill in the affected regions in all views consistently, or choose from many possible ways to indicate the same body region. Many of the problems associated with the existing body region indication systems arise from the static nature of the outline templates.

SUMMARY

In general, the invention is directed toward techniques for allowing a user to indicate regions on the human body. Specifically, a body region indication device according to the invention displays two-dimensional, dynamic body image templates to the user, and the user indicates regions on the body templates that correspond to affected regions of a patient's body. The body region indications may correspond to locations of injury, pain, treatment, discoloration, paresthesia, or the like. The user may be the patient, a nurse, a clinician or a physician.

The body image templates illustrate views of an external surface of a human body at various rotations about an axis. The degree of rotation about the axis for each of the body image templates may be determined by a predetermined value, a user selection, or an adaptive computer system. In exemplary embodiments, a user controls display of the templates, which may allow the user to perceive rotation of a three-dimensional body surface about an axis.

The two-dimensional user indicated regions from each of the displayed body image templates are stored in a body surface coordinate system that describes points on a body surface. The body surface coordinate system may be a three-dimensional or two-dimensional coordinate system. The device may generate the body image templates from the coordinate system using, for example, three-dimensional polygon rendering techniques known in the art. In some embodiments, the views provided by each template are partially overlapping. In such embodiments, a user indicated region from the first body template located in the overlapping area is also displayed on the second body template.

The device includes a display for displaying the body image templates. In some embodiments, the display is a touch-screen display for receiving indications of regions of body image templates from the user. In exemplary embodiments, the device is a programming device used by a clinician, and in some cases the patient, during a programming session for programming an implantable medical device that delivers neurostimulation therapy to the patient. The device may include a memory to store coordinate systems that include body region indication information for one or more patients, and may regenerate body image templates from a selected one of the stored coordinate systems to, for example, allow a clinician to review patient symptoms at some later time.

In one embodiment, the invention is directed to a method in which a plurality of two-dimensional body templates are sequentially displayed, with each of the body templates illustrating a view of an external surface of a human body rotated an angle about an axis.

In another embodiment, the invention is directed to a computer-readable medium containing instructions that cause a programmable processor to sequentially display a plurality of two-dimensional body templates, each of the body templates illustrating a view of an external surface of a human body rotated an angle about an axis.

In another embodiment, the invention is directed to a device comprising a display and a processor. The processor sequentially displays a plurality of two-dimensional body templates via the display, each of the body templates illustrating a view of an external surface of a human body rotated an angle about an axis.

In a further embodiment, the invention is directed to a method comprising displaying a two-dimensional body template that illustrates a view of an external surface of a human body, receiving input from a user indicating a region of the body template, and mapping the input to a body surface coordinate system that describes the external surface of the human body.

In an additional embodiment, the invention is directed to a computer-readable medium containing instructions that cause a programmable processor to display a two-dimensional body template that illustrates a view of an external surface of a human body, receive input from a user indicating a region of the body template, and map the input to a body surface coordinate system that describes the external surface of the human body.

In another embodiment, the invention is directed to a device comprising a display to display a two-dimensional body template that illustrates a view of an external surface of a human body, a user input circuit to receive input from a user indicating a region of the body template, and a memory to store a body surface coordinate system that describes the representation of the external surface of the human body. The device further comprises a processor to display the body template via the display, and map the user input to the body surface coordinate system.

The invention may provide a number of advantages. For example, sequential presentation of a series of body image templates that depict rotation of a body surface about an axis may allow a user to remain better oriented with respect to whether limbs and the like are "right" or "left." The device may allow a user to control the direction, and, in some cases, the extent of rotation, which may further improve the orientation of the user.

The body image templates may overlap, such that no portion of the body surface is not depicted by a body image template. In such embodiments, the device may display a region indicated on one body template in subsequent templates, which may allow the user to give more accurate region indications due to the persistent nature of the body region indications. The accurate indications may improve the usability of body region indications for physicians or clinicians in aiding diagnosis and treatment of the patient, such as aiding in the determination of efficacy of purposed neurostimulation as evaluated based on overlap between indicated regions of pain and paresthesia. Users may find indicating body regions on a representation of a sequentially rotating body surface to be intuitive, particularly in embodiments where the body image templates overlap and are generated to redisplay previously indicated body regions.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 2A through D are schematic diagrams illustrating another example body region indication device displaying body image templates corresponding to four views of a body.

DETAILED DESCRIPTION

Figure 1A:
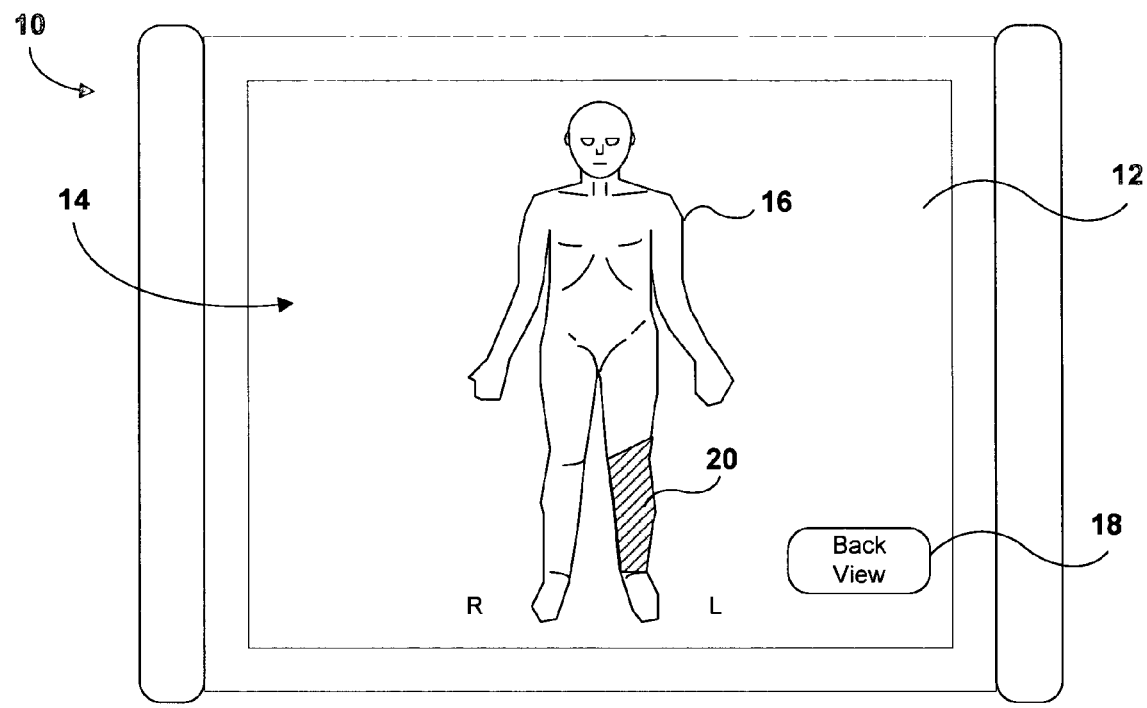
FIGS. 1A and 1B are schematic diagrams illustrating an example body region indication device displaying body image templates corresponding to two views of a body.
Figure 1B:
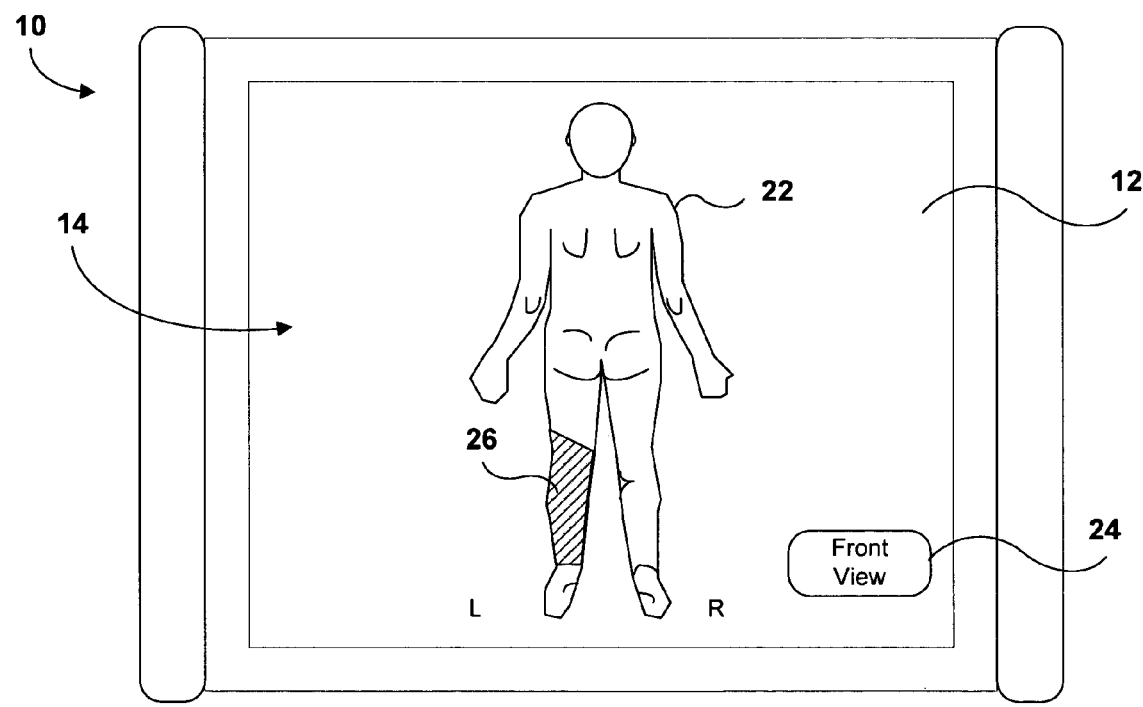

FIGS. 1A and 1B are schematic diagrams illustrating an example body region indication device 10. In the illustrated example, indication device 10 displays body image templates 16 and 22, which correspond to two views of the surface a human body. In this case, indication device 10 is a handheld computing device that may be used by a user, such as a patient, a nurse, a clinician, or a physician, to indicate regions of the human body. More specifically, indication device displays body view templates 16 and 22 to allow the user to indicate regions of injury, pain, treatment, discoloration, paresthesia, or the like experienced by the patient.

Indication device 10 includes a display 12, and provides a graphical user interface (GUI) 14 via display 12. In FIG. 1A, GUI 14 includes a front view template 16, e.g., an image illustrating a front view of the surface of the human body, and a back view selection button 18. In FIG. 1B, GUI 14 includes a back view template 22, e.g., an image illustrating a back view of the surface of the human body, and a front view selection button 24. Front and back view selection buttons 18 and 24 allow the user to switch between front view and back view templates 16 and 22.

The user may provide information to indication device 10 by interacting with GUI 14. The user may use GUI 14 to, for example, enter patient information, indicate body regions on body image templates 16 and 22, and switch between body image templates 16 and 22 using buttons 18 and 24. Display 12 may comprise a touch screen that allows the user to interact with GUI 14 using a stylus (not shown). In other embodiments, indication device 10 may be coupled to a keyboard or other pointing device, such as a mouse, to enable user input.

In exemplary embodiments, indication device 10 is a programming device used by a clinician to generate one or more programs that control the delivery of neurostimulation by an implantable medical device that is implanted within the patient. A neurostimulation therapy program includes parameters that define the neurostimulation delivered by the implantable medical device. For example, where the implantable medical device delivers neurostimulation as pulses via selected electrodes from a set of electrode implanted in the patient, a neurostimulation program may define a voltage or current pulse amplitude, and a pulse width and rate, and may identify the selected electrodes. A number of programs may be tested during a programming session, and one or more programs may be selected from those tested for long-term use by the patient.

During programming the clinician and/or the patient may use indication device 10 to indicate the regions of pain experienced by the patient which the neurostimulation is to treat, and regions of paresthesia experienced by the patient in response to delivery of each program. The overlap of the paresthesia resulting from each program with the pain may be used to "score" the programs. Further details regarding such methods of evaluating neurostimulation therapy programs may be found in U.S. Pat. No. 6,308,102, issued to Sieracki et al.

Indication device 10 displays the two-dimensional front-view template 16 to the user via display 12, and may also, as shown in FIGS. 1A and 1B, display left and right side markers via display 12 so as to allow the user to understand the orientation of template 16. The user enters first region indication 20 into indication device 10 by shading or outlining a region corresponding to an affected body region of the patient. After receiving first indication 20, indication device 10 redisplays front view template 16 with shading to illustrate first region indication 20.

Indication device 10 stores information reflecting first region indication 20 as part of a body surface coordinate system. In some embodiments, the body surface coordinate system is a three-dimensional map of the external surface of the human body, e.g., defines points of a representative human body surface with three coordinates. In other embodiments, the body surface coordinate system is a two-dimensional map of a mathematically peeled and flattened external surface of the human body, e.g., defines points of a representative human body surface with two coordinates. In either case, indication device 10 stores information in association with the points that reflects whether those points have been indicated by the user.

Once the user has entered all body regions corresponding to the patient's symptoms on front view template 16, the user may select back view template 22 for display by selecting back view selection button 18. Selecting back view selection button 18 causes indication device 10 to display back view template 22, as in FIG. 1B. As indication device 10 displays back view template 22, it may also display any portion of first region indication 20 that overlaps onto back view template 22. In other words, use of a coordinate system to store information describing region indication 20, allows region indication 20 to be at least partially redisplayed on other body view templates that overlap front view template 16. In the case where there are only two body views, as shown in FIGS. 1A and 1B, and first region indication 20 includes the edges of front view template 16, a portion of first region indication 20 may be redisplayed at the edges of back view template 22.

As shown in FIGS. 1A and 1B, indication device 10 may display back view template 22 with left and right side markers to allow the user to understand the orientation of back view template 22. The user may input second region indication 26 by shading or outlining a region corresponding to an affected body region of the patient. Second region indication 26 may be an addition to the displayed portion of first region indication 20. After receiving second region indication 26, indication device 10 redisplays back view template 22 with shading to illustrate second region indication 26. Indication device 10 stores second region indication 26 in the body surface coordinate system along with first region indication 20. The single coordinate system allows region indication 26 to be at least partially redisplayed on other body view templates that overlap back view template 22.

Once the user has entered all body regions corresponding to the patient's symptoms on back view template 22, the user may select to view front view template 16 again. Selecting front view selection button 24 from GUI 14 causes indicator device 10 to again display front view template 16 with first indication region 20 and any overlapping indications from back view template 22 illustrated.

The user may switch between the front view template 16 and the back view template 22 via front and back view selection buttons 18 and 24 as many times as necessary to indicate all the regions corresponding to the patient. First and second region indications 20, 26 may be manipulated multiple times. Each change in the indication regions is reflected in the body coordinate system and illustrated on the redisplayed body template.

FIGS. 2A through D are schematic diagrams illustrating another example body region indication device 30 displaying body image templates 36, 42, 48 and 50, corresponding to four views of a body. Like indication device 10 of FIGS. 1A and 1B, indication device 30 is a handheld computing device that may be used by a user, such as a patient, a nurse, a clinician, or a physician, to indicate regions of injury, pain, treatment, discoloration, paresthesia, or the like experienced by the patient. Indication device 30 includes a display 32, and may provide a GUI 34 via display 32. Indication device 30 may operate in a substantially similar manner as indication device 10 described with reference to FIGS. 1A and 1B.

In FIG. 2A, GUI 34 includes a front view template 36, a left view selection button 38, and a right view selection button 39. In FIG. 2B, GUI 34 includes a right view template 42, a front view selection button 44, and a back view selection button 45. In FIG. 2C, GUI 34 includes a back view template 48, the left view selection button 38, and the right view selection button 39. In FIG. 2D, GUI 34 includes a left view template 50, the front view selection button 44, and the back view selection button 45.

Front view template 36 of FIG. 2A is substantially similar to front view template 16 of FIG. 1A. The user inputs region indication 40 into indication device 30 by shading or outlining a region on the displayed front view template 36 that corresponds to an affected body region of the patient. After receiving indication 40, indication device 30 redisplays front view template 36 with shading to illustrate region indication 40 via display 32. Indication device 30 stores region indication 40 in a body surface coordinate system as described above with reference to FIGS. 1A and 1B. When the user is ready to view additional body templates, the user may select either left view selection button 38 or right view selection button 39 from GUI 34. Selecting left view selection button 38 causes indicator device 30 to display left view template 50, shown in FIG. 2D, and selecting right view selection button 39 causes indicator device 30 to display right view template 42, shown in FIG. 2B. Along with left or right view templates 50 and 42, indicator device 30 displays any portion of region indication 40 that overlaps onto left or right view templates 50 and 42.

As shown in FIG. 2B, right view template 42 is displayed for indication device 30 to accept region indications (not shown in FIG. 2B) from the user. All indicated regions are stored in the body surface coordinate system along with region indication 40. The user may select front view selection button 44 or back view selection button 45 when ready to view additional body templates.

FIG. 2C illustrates back view template 48, which is substantially similar to back view template 22 from FIG. 1B. Region indications may be entered by the user onto back view template 48 and then stored in the coordinate system. The user may choose to view either right view template 42 or left view template 50 via the body view selection buttons 38 and 39.

In FIG. 2D, left view template 50 is displayed along with a portion of region indication 40. As shown in FIG. 2A, region indication 40 is shaded to the left edge of front view template 36, so a portion of indication 40 overlaps onto left view template 50. The user may enter new region indications and add onto region indication 40 on left view template 50. The region indications are stored in the coordinate system. The user may then select front view selection button 44 or back view selection button 45 to redisplay previously displayed body views.

The user may switch between the four body view templates 36, 42, 48, and 50 via the body view selection buttons 38, 39, 44, and 45 as many times as necessary to indicate all the regions corresponding to the patient's symptoms. Region indication 40 and other region indications (not shown) may be manipulated multiple times. Each change in the indication regions is reflected in the body coordinate system and illustrated on the redisplayed body templates 36, 42, 48 and 50.

Figure 3:
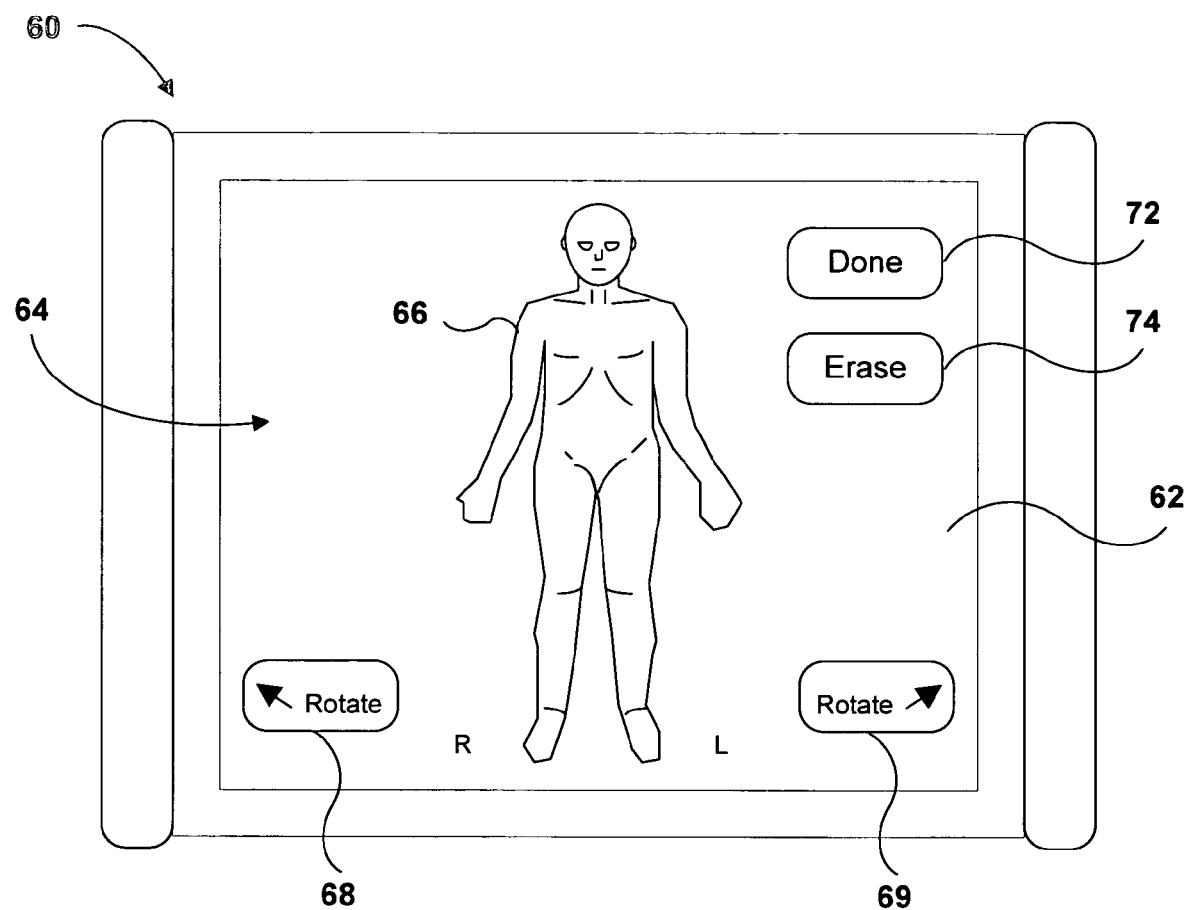
FIG. 3 is a schematic diagram illustrating another example body region indication device displaying a body image template.

FIG. 3 is a schematic diagram illustrating another example body region indication device 60 displaying a body image template 66. Indication device 60 operates in a substantially similar manner to indication device 10, which was described above with reference to FIGS. 1A and 1B. Indication device 60 includes a display 62, and provides a GUI 64 via display 62. GUI 64 includes a body view template 66, a left rotation button 68, a right rotation button 69, a done button 72, and an erase button 74. As shown in FIG. 3, indication device 60 is a handheld computer, which in some embodiments may be a programming device for programming an implantable medical device.

Indication device 60 displays body view template 66 via display 62 to allow a user, such as a patient, a nurse, a clinician, or a physician, to enter region indications that correspond to affected body regions of the patient. Body view template 66 represents a view of an external surface of a human body. In FIG. 3, body view template 66 represents a front body view. The entered indications (not shown) are stored in a body surface coordinate system that maps the external surface of the human body as described in reference to FIGS. 1A and 1B. After each region indication, indication device 60 redisplays body view template 66 with the indicated region illustrated on the template 66.

In order to enter additional region indications or extend previously entered region indications on a different body template (not shown), the user selects left rotation button 68 or right rotation button 69. Selecting one of the rotation direction buttons 68 or 69 causes indication device 60 to display a body template that represents a different view of the external body surface, i.e., a view that is rotated an angle from the view presented by template 66. A degree of rotation represented by the subsequent body view may be a predetermined amount.

The user may hold down one of buttons 68 and 69 to rotate through a number of templates, which may allow the user to perceive that the user is rotating a three-dimensional representation of the external body surface. However, indication device 60 need not display all possible body view templates. Rather, indication device 60 need only display a sufficient number of body view templates to maintain user orientation to the rotations. Nonetheless, it is preferred to display sufficient body templates to create an apparently smooth rotation of the external body surface.

As shown in FIG. 3, the user may select erase button 74 to remove previously entered region indications. Selecting erase button 74 may cause all region indications illustrated on displayed body view template 66 to be erased, or may allow the user to select regions to be erased by shading or outlining the regions to be erased. The ability to erase and retouch entered region indications increases accuracy of the region indications. Each change in the region indications is reflected in the body coordinate system and illustrated on the redisplayed body templates. The user may signify when the region indications are complete by selecting done button 72. Selecting done button 72 stops indication device 60 from accepting any further region indications or body view rotation selections.

In some embodiments, indication device 60 may sequentially display additional body views according to a display time limit. In that case, the user may enter region indications on one of the body templates for a preset period of time. Indication device 60 displays the next body template once the time limit has expired. The rotation of the body templates may continue for a set number of revolutions or until the user specifies the region indications are complete.

In some embodiments, indication device 60 may adaptively determine which template to display based on the region indications input by the user. For example, indication device 60 may select and/or generate a template corresponding to a degree of rotation of the external body surface that is determined based upon the location of the region indications entered by the user within a template. For example, a region indication shaded to the edge of a displayed body template may cause indication device 60 to select and/or generate a next body template that represents a small rotation of the body surface, to allow the user to accurately complete the region. On the other hand, a region indication that remains substantially far away from an edge of a current body template may cause indication device 60 to display a next body template that represents a larger degree of rotation, to allow the user to begin indicating another region. Using such an indication device 60, the user may be able to give accurate indications with fewer body templates.

Figure 4:
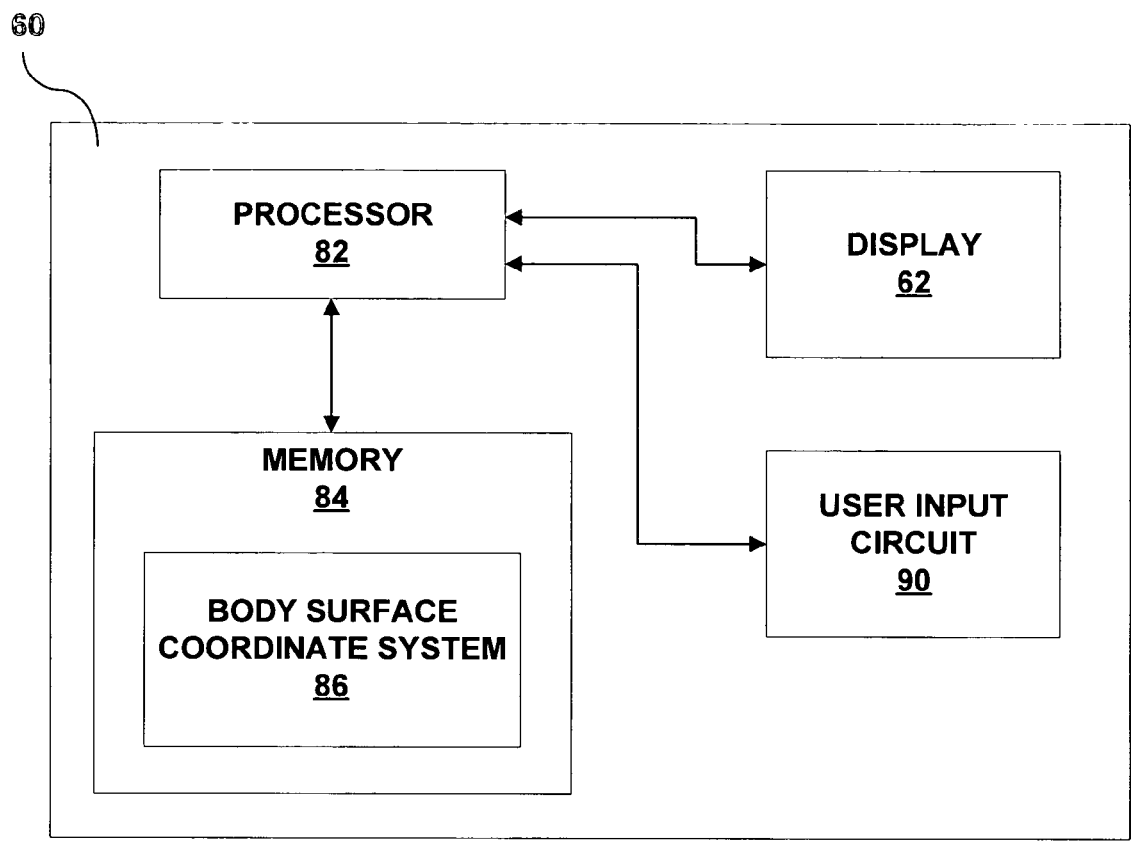
FIG. 4 is a block diagram illustrating the body region indication device of FIG. 3 in greater detail.

FIG. 4 is a block diagram illustrating the body region indication device of FIG. 3 in greater detail. Indication device 60 includes a processor 82, a memory 84 that stores a body surface coordinate system 86, a display 62, and a user input circuit 90. Although FIG. 4 illustrates indication 60, it is understood that indication devices 10 and 30 of FIGS. 1A and 1B, and 2A through D may include similar components and provide similar functionality.

Processor 82 controls indication device 60 to provide functionality as described herein. In particular, processor 82 displays body templates via display 62, and receives input from a user via user input circuit 90. The user input may include body region indications, body view or rotation selections, erase selections, done selections, and responses to a prompts. Processor 82 stores information reflecting received body region indications and erase selections in body surface coordinate system 86 within memory 84. In some embodiments, memory 84 stores one or more coordinate systems 86 that include body region indication information for one or more patients, and may regenerate body image templates from a selected one of the stored coordinate systems to, for example, allow a clinician to review patient symptoms at some later time.

The displayed body templates are two-dimensional views of an external surface of a human body. Based on user input of body view or rotation selections, processor 82 may generate a body template, or may retrieve a previously generated body template that may be stored in memory 84. In exemplary embodiments, processor 82 generates body templates from body surface coordinate system 86, and regenerates body templates upon receiving region indications from the user to reflect the region indication information stored in coordinate system 86. Processor 82 may generate body image templates from coordinate system 86 using, for example, three-dimensional polygon rendering techniques that include hidden-line removal.

The invention, however, is not so limited. In some embodiments, body templates are not generated based on coordinate system, and are not generated by processor 82. Body templates may be generated using any means known in the art for generating a two-dimensional image, and may, for example, be pre-stored in memory 86, or received by indication device 60 via a network connection or removable media (not shown). Regeneration of body templates to display regions indicated by a user may include superimposing a graphical depiction of the indicated region on a body image template as displayed via display 62.

Indication device 60 may receive body region indications via user input circuit 90 as two-dimensional polygon outlines of the user indicated regions on a body image template. The body region indications may be translated into coordinates of body surface coordinate system using known geometric transforms and/or interpolation techniques. For example, in exemplary embodiments, a third coordinate to each point within an indicated region. In some embodiments, display 62 may comprise a touch screen that enables the user to enter region indications directly on the displayed body image template using a stylus. In such cases, user input circuit 90 is included as part of display 62.

In exemplary embodiments, body surface coordinate system 86 is a three-dimensional coordinate system. To create such a three-dimensional coordinate system, a representation of the external surface of the human body is intersected with three orthogonal axes and embedded in a cube of space. Coordinates for points on the surface, e.g., vertex points, are stored as body surface coordinate system 86.

Valid region indication coordinates are required to lie within the polyhedral surface defined by the three-dimensional body surface coordinate system 86. The coordinates can be checked by linearly interpolating between vertex points of the body surface coordinate system. In some embodiments, region indications are stored as information associated with the three coordinates for each point included in the indicated region. In embodiments where body image templates are generated from body surface coordinate system 86, increasing the density of vertices increases the curved appearance of the body template templates. Curve-smoothing spline and other higher-order interpolations can also or alternatively be used to increase the natural appearance of the body image templates.

In some embodiments, body surface coordinate system 86 is a two-dimensional coordinate system. To create a two-dimensional coordinate system, the external surface of a representative human body is mapped to a plane by mathematically pealing and flattening the surface. The resulting map contains special indications to maintain continuity across the edges of the flattened map. For example, the circumference of the body trunk and limbs become planer regions with the "left edge" noted as continuing into the "right edge."

Use of a two-dimensional body surface coordinate system 86 may allow for a compression of data in that only two coordinates are required to identify points of the body surface, and calculations may be done on a two-dimensional body surface coordinate system 86 using two-dimensional rather than three-dimensional operations. In some embodiments, indication device 60 generates body image templates directly from a two-dimensional body surface coordinate system, while in other embodiments indication device 60 may project coordinate system 86 into a three-dimensional coordinate system and generate the body image templates from the three-dimensional coordinate system. In other words, where processor 82 generates the body image templates from body surface coordinate system 86, processor 82 may generate body image templates from a three-dimensional coordinate system, e.g., using three-dimensional polygon rendering techniques as described above, regardless of which type of body surface coordinate system 86 is used by indication device 60.

In embodiments where indication device 60 uses a two-dimensional body surface coordinate system 86 for storage of body region indication information and uses a three-dimensional coordinate system for generation of body image templates, the three-dimensional body surface need not be stored in memory 84. Instead, processor 82 may first generate the three-dimensional coordinate system from the two-dimensional coordinate system 86 each time that body image templates are to be generated and displayed or regenerated and redisplayed. Processor 82 may then generate the individual two-dimensional body templates for display from the three-dimensional coordinate system using three-dimensional polygon rendering techniques. Any stored region indications may be mapped from the two-dimensional coordinate system to the three-dimensional coordinate system and then illustrated with shading on the displayed two-dimensional body templates using three-dimensional polygon rendering techniques.

Processor 82 may include one or more of a microprocessor, a controller, a digital signal processor (DSP), an application specific integrated circuit (ASIC), a field-programmable gate array (FPGA), discrete logic circuitry, or the like. In addition to body surface coordinate system 86 memory 84 may store program instructions that, when executed by processor 82, cause indication device 80 to perform the functions ascribed to indication device 80 herein. Memory 84 may include any volatile, non-volatile, fixed, removable, magnetic, optical, or electrical media, such as a random access memory (RAM), read-only memory (ROM), CD-ROM, hard disk, removable magnetic disk, memory cards or sticks, non-volatile RAM (NVRAM), electrically-erasable programmable ROM (EEPROM), flash memory, and the like.

Figure 5:
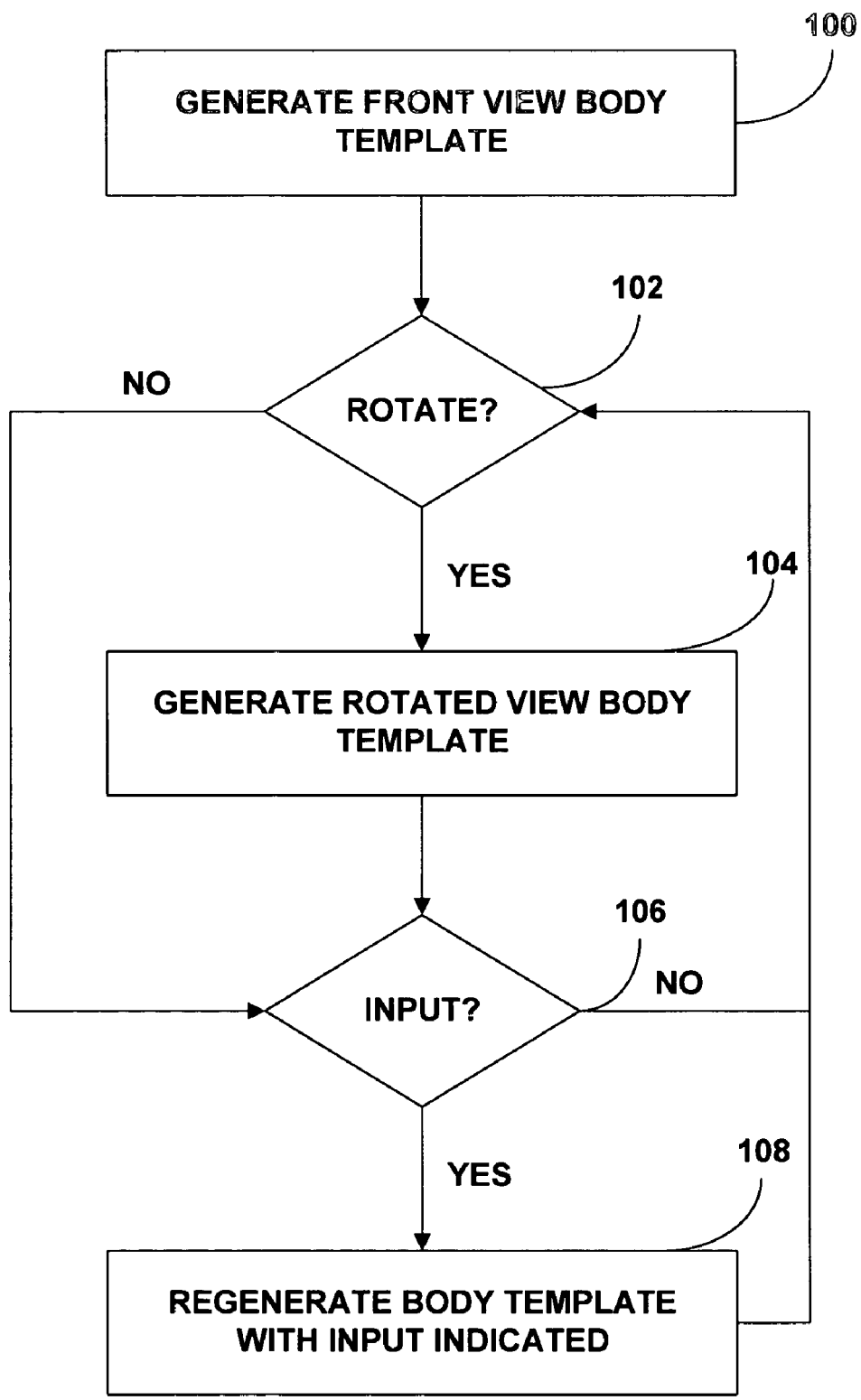
FIG. 5 is a flow diagram illustrating a method that may be employed by a body region indication device to display body image templates.

FIG. 5 is a flow diagram illustrating a method that may be employed by a body region indication device, such as body region indication device 60, to display body image templates. Indication device 60 generates a first body view template, such as front view template 66 (100) from a body surface coordinate system 86 that maps an external surface of a human body, and displays front view template 66 to a user via display 62. Coordinate system 86 may be a three-dimensional or two-dimensional coordinate system, as described above.

The user may choose to rotate front view template 66 (102) by selecting one of rotation direction buttons 68 and 69. If the user chooses to rotate front view template 66 then indication device 60 generates a rotated body template (104) from coordinate system 86 that represents a rotation of a three-dimensional external body surface from the front view. The rotated body image template is then displayed to the user.

The user may also input region indications (106) that corresponds to an affected body region of a patient on front view template 66, or any other body image template selected using rotation direction buttons 68 and 69. Indication device 60 receives the user input and regenerates the displayed body image template to illustrate the region indication (108), and displays the regenerated body template to the user via display 62. The input region indication may be stored in coordinate system 86, as will be described in greater detail below.

As illustrated in FIG. 5, the user may rotate maps and input region indications as necessary to fully and accurately identify the effected body regions of the patient. Although not illustrated in FIG. 5, the user may erase all or portions of previously input region indications using erase button 74 (FIG. 3). The user may use done button 72 to indicate that the user has completed inputting region indications. The coordinate system 86 containing information describing the input region indication(s) may be, for example, stored as part of a patient record, or used to "score" a neurostimulation therapy program during a programming session.

Figure 6:
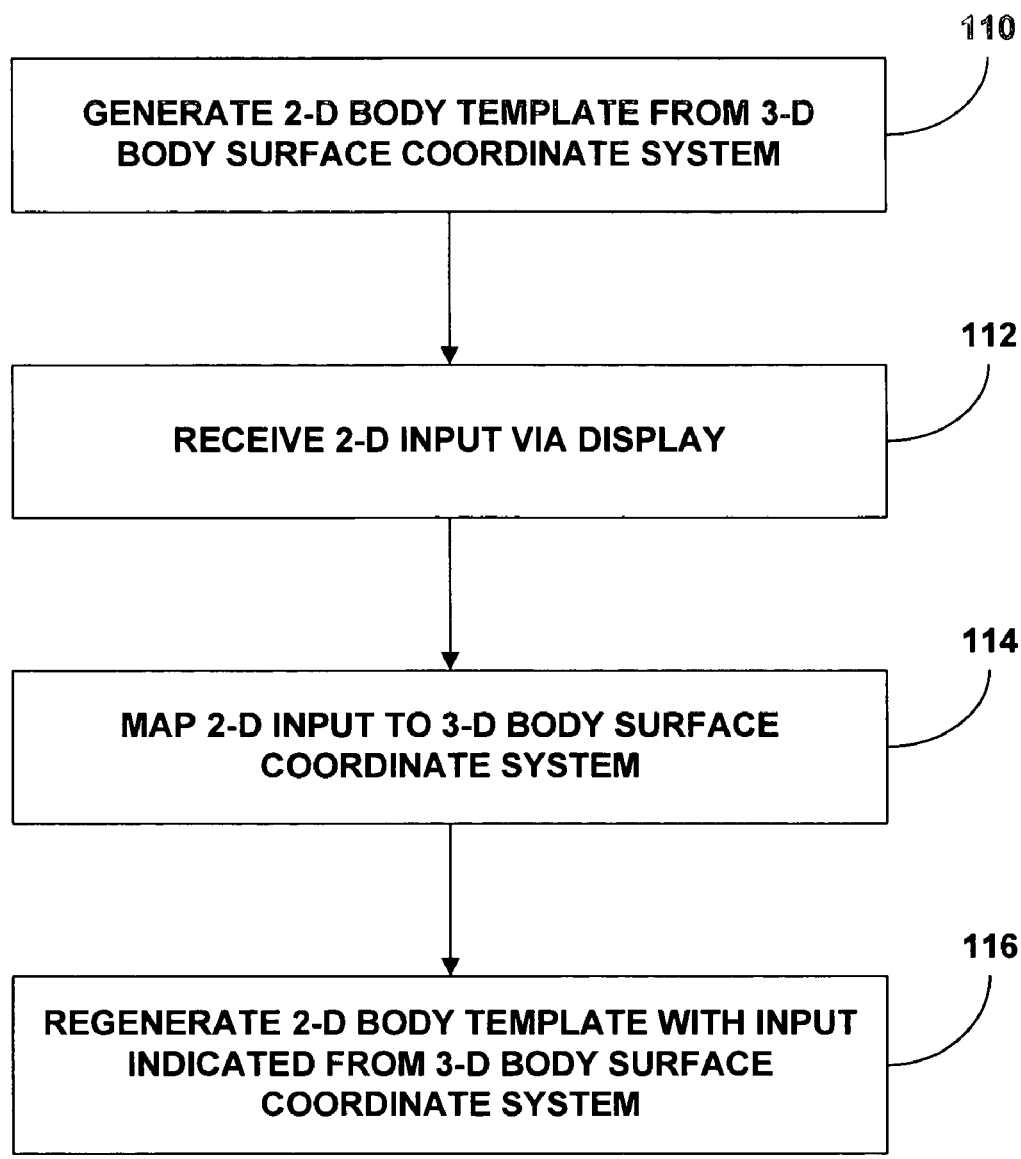
FIG. 6 is a flow diagram illustrating a method that may be employed by a body region indication device to map user input indicating regions of a body image template to a three-dimensional body surface coordinate system.

FIG. 6 is a flow diagram illustrating a method that may be employed by body region indication device 60 to map user input indicating regions of a body image template to a three-dimensional body surface coordinate system 86. As described above, three-dimensional body surface coordinate system 86 maps an external surface of a human body and is stored in a memory 84 within indication device 60. A processor 82 within indication device 60 generates a two-dimensional body view template from three-dimensional coordinate system 86 (110). The body template is displayed via a display 62 by processor 82.

Processor 82 receives a region indication on the displayed body template from a user via display 88 (112). Processor 82 maps the received two-dimensional input to three-dimensional coordinate system 86 (114) to store in memory 84. Processor 82 then regenerates the two-dimensional body template along with the region indication from three-dimensional coordinate system 86 (116). The regenerated body template is redisplayed with shading to illustrate the region indication.

Figure 7:
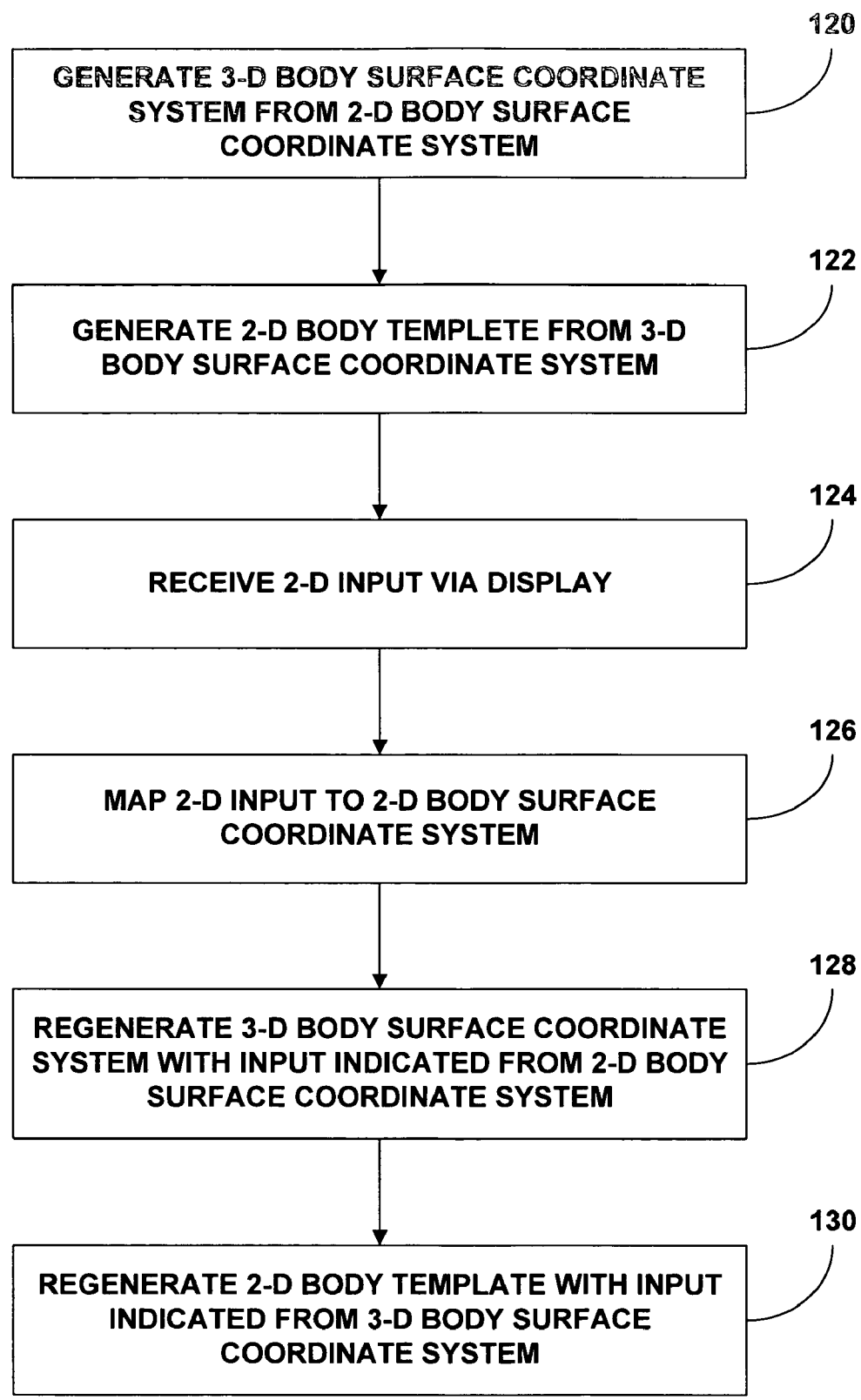
FIG. 7 is a flowchart illustrating a method that may be employed by a body region indication device to map user input indicating regions of a body image template to a two-dimensional body surface coordinate system.

FIG. 7 is a flowchart illustrating a method that may be employed by body region indication device 60 to map user input indicating regions of a body image template to a two-dimensional body surface coordinate system 86. Two-dimensional body surface coordinate system 86 maps a pealed and flattened external surface of a human body and is stored in a memory 84 within indication device 80. A processor 82 within indication device 80 generates a three-dimensional body surface coordinate system from two-dimensional coordinate system 86 (120) that represents the curved surface of the human body. Processor 82 then generates a two-dimensional body view template from the three-dimensional coordinate system (122). The body template is displayed via a display 62 by processor 82.

Processor 82 receives a region indication on the displayed body template from a user via display 62 (124). Processor 82 maps the received two-dimensional input directly to the two-dimensional coordinate system 86 (126) to store in memory 84. Processor 82 regenerates the three-dimensional coordinate system from two-dimensional coordinate system 86 (128), and maps the stored region indication from two-dimensional coordinate system 86 to the three-dimensional coordinate system. Processor 82 then regenerates the two-dimensional body template along with the region indication from the three-dimensional coordinate system (130). The body template is redisplayed with shading to illustrate the region indication. Processor 82 may generate the three-dimensional coordinate system from two-dimensional body surface coordinate system 86 as needed, e.g., the three-dimensional coordinate system need not be persistently stored in memory 84.

Various embodiments of the invention have been described. However, one skilled in the art will appreciate that various modifications may be made to these embodiments without departing from the scope of the invention. For example, although region indication devices have been described herein as programming devices for programming neurostimulation therapy delivered by an implantable medical device, the invention is not so limited. Region indication devices as described herein may be included as part of programming devices for any of a number of types of implantable medical devices, such as cardiac pacemakers and implantable pumps.

In some embodiments, region indication devices may simply take the form of a medical device used for identification, and in some cases recordation, of an affected region on a patient's body. Such a medical device may be useful, for example during an initial examination and/or interview of a patient at a clinic, emergency, or at the scene of an emergency responded to by paramedics. These medical devices may be used to locate and scale pain sensations, describe regions of skin discoloration or sensitivity, or pinpoint exact areas of injury. The indication device may be able to receive several types of input in addition to those described herein depending on the application for which the device is employed. These and other embodiments are within the scope of the following claims.

The invention claimed is:

1. A method comprising:
   sequentially displaying a plurality of two-dimensional body templates, each of the body templates illustrating a view of an external surface of a human body rotated an angle about an axis;
   receiving input from a user indicating a region of one of the body templates;
   mapping the input to a body surface coordinate system that describes a plurality of points on the external surface of the human body;
   regenerating the body template to illustrate the indicated region on the template based on the body surface coordinate system with the mapped input; and
   displaying the regenerated body template.

2. The method of claim 1, wherein the plurality of body templates comprises a front view template and a back view template.

3. The method of claim 1, wherein the plurality of body templates comprises a front view template, a right-side view template, a back view template, and a left-side view template.

4. The method of claim 1, wherein the regenerated body template is a first one of the body templates that illustrates a portion of the surface, the method further comprising:
   generating a second one of the body templates to illustrate at least some of the portion of the surface illustrated by the first one of the body templates and at least a portion of the region indicated by the user based on the body surface coordinate system with the mapped input; and
   displaying the second one of the body templates.

5. The method of claim 1, wherein sequentially displaying the body templates comprises sequentially displaying the body templates according to commands received from the user.

6. The method of claim 5, wherein sequentially displaying the body templates according to commands received from the user comprises displaying the body templates according to commands received via at least one direction arrow.

7. The method of claim 5, wherein sequentially displaying the body templates according to commands received from the user comprises:
   displaying a first one of body templates;
   receiving a command from the user;
   generating a second one of the body templates in response to the command; and
   displaying the second one of the body templates.

8. The method of claim 1, wherein sequentially displaying the body templates comprises sequentially displaying the body templates via a display, and receiving input from a user comprises receiving input from the user via the display.

9. The method of claim 1, wherein sequentially displaying the body templates comprises:
   displaying a first one of the body templates;
   generating a second one of the body templates to illustrate a view of the external surface of the human body, wherein the angle of rotation of the surface about the axis is based on a proximity of the received body region indication to an edge of the first one of the body templates; and
   displaying the second one of the body templates.

10. The method of claim 1, wherein the input comprises a two-dimensional polygon outline of the indicated region.

11. The method of claim 1, further comprising generating each of the body templates based on the body surface coordinate system.

12. The method of claim 1, wherein the body surface coordinate system comprises a three-dimensional coordinate system.

13. The method of claim 12, further comprising generating the three-dimensional coordinate system by applying one of a linear interpolation, a higher-order interpolation, or a spline technique to determine valid body coordinates.

14. The method of claim 12, wherein mapping the input into a three-dimensional body surface coordinate system comprises assigning a third coordinate to each point of the indicated region of the body template.

15. The method of claim 1, wherein the body surface coordinate system comprises a two-dimensional coordinate system.

16. The method of claim 15, further comprising generating the two-dimensional coordinate system by mathematically peeling and flattening a representation of the external surface of the human body, and indicating continuity at edges of the body surface.

17. The method of claim 15, wherein displaying the regenerated body template comprises projecting the two-dimensional coordinate system onto a three-dimensional frame representation of the external surface of the human body.

18. The method of claim 1, wherein regenerating the one of the body templates to illustrate the indicated region on the template comprises regenerating the one of the body templates to include shading of the indicated region on the template.

19. The method of claim 1, wherein the body region indication indicates a region of at least one of pain or paresthesia experienced by a patient.

20. The method of claim 1, wherein the user comprises one of a patient or a clinician.

21. The method of claim 1, wherein the axis comprises a vertical axis through a center of the body.

22. The method of claim 1, wherein each of the body templates illustrates a view of the external surface of the human body rotated an angle about at least one of a plurality of axes.

23. A computer-readable storage medium storing instructions that cause a programmable processor to:
    sequentially display a plurality of two-dimensional body templates, each of the body templates illustrating a view of an external surface of a human body rotated an angle about an axis;
    receive input from a user indicating a region of one of the body templates;
    map the input to a body surface coordinate system that describes a plurality of points on the external surface of the human body;
    regenerate the one of the body templates to illustrate the indicated region on the template based on the body surface coordinate system with the mapped input; and
    display the regenerated body template.

24. The computer-readable storage medium of claim 23, wherein the plurality of body templates comprises a front view template and a back view template.

25. The computer-readable storage medium of claim 23, wherein the plurality of body templates comprises a front view template, a right-side view template, a back view template, and a left-side view template.

26. The computer-readable storage medium of claim 23, wherein the regenerated body template is a first one of the body templates that illustrates a portion of the surface, the computer-readable medium further comprising instructions that cause a programmable processor to:
    generate a second one of the body templates to illustrate at least some of the portion of the surface illustrated by the first one of the body templates and at least a portion of the region indicated by the user based on the body surface coordinate system with the mapped input; and
    display the second one of the body templates.

27. The computer-readable storage medium of claim 23, wherein the instructions that cause a programmable processor to sequentially display the body templates comprise instructions that cause a programmable processor to display the body templates according to commands received from the user.

28. The computer-readable storage medium of claim 27, wherein the instructions that cause a programmable processor to sequentially display the body templates according to commands received from the user comprise instructions that cause a programmable processor to display the body templates according to commands received via at least one direction arrow.

29. The computer-readable storage medium of claim 27, wherein the instructions that cause a programmable processor to sequentially display the body templates according to commands received from the user comprise instructions that cause a programmable processor to:
    display a first one of the body templates;
    receive a command from the user;
    generate a second one of the body templates according to the command; and
    display the second one of the body templates.

30. The computer-readable storage medium of claim 23, wherein the instructions that cause a programmable processor to sequentially display the body templates and receive input from a user comprise instructions that cause a programmable processor to sequentially display the body templates and receive the input via a display.

31. The computer-readable storage medium of claim 23, wherein the instructions that cause a programmable processor to sequentially display the body templates comprise instructions that cause a programmable processor to:
    display a first one of the body templates;
    generate a second one of the body templates to illustrate a view of the external surface of the human body, wherein the angle of rotation of the surface about the axis is based on a proximity of the received body region indication to an edge of the first one of the body templates; and
    display the second one of the body templates.

32. The computer-readable storage medium of claim 23, wherein the input comprises a two-dimensionial polygon outline of the indicated region.

33. The computer-readable storage medium of claim 23, further comprising instructions that cause a programmable processor to generate each of the body templates based on the body surface coordinate system.

34. The computer-readable storage medium of claim 23, wherein the body surface coordinate system comprises a three-dimensional coordinate system.

35. The computer-readable storage medium of claim 34, further comprising instructions that cause a programmable processor to generate the three-dimensional coordinate system by applying one of a linear interpolation, a higher-order interpolation, or a spline technique to determine valid body coordinates.

36. The computer-readable storage medium of claim 23, wherein the instructions that cause a programmable processor to map the input into a three-dimensional body surface coordinate system comprise instructions that cause a programmable processor to assign a third coordinate to each point of the indicated region of the body template.

37. The computer-readable storage medium of claim 23, wherein the body surface coordinate system comprises a two-dimensional coordinate system.

38. The computer-readable storage medium of claim 37, further comprising instructions that cause a programmable processor to generate the two-dimensional coordinate system by mathematically peeling and flattening a representation of the external surface of the human body, and indicating continuity at edges of the body surface.

39. The computer-readable storage medium of claim 37, wherein the instructions that cause a programmable processor to display the regenerated body template comprise instructions that cause a programmable processor to project the two-dimensional coordinate system onto a three-dimensional frame representation of the external surface of the human body.

40. The computer-readable storage medium of claim 23, wherein the instructions that cause a programmable processor to regenerate the one of the body templates to illustrate the indicated region on the template comprise instructions that cause a programmable processor to regenerate the one of the body templates to include shading of the indicated region on the template.

41. The computer-readable storage medium of claim 23, wherein the axis comprises a vertical axis through a center of the body.

42. The computer-readable storage medium of claim 23, wherein each of the body templates illustrates a view of the external surface of the human body rotated an angle about at least one of a plurality of axes.

43. A device comprising:
a display;
a memory that stores a body surface coordinate system that describes a plurality of points on an external surface of a human body; and
a processor to sequentially display a plurality of two-dimensional body templates via the display, each of the body templates illustrating a view of the external surface of the human body rotated an angle about an axis, receive input from a user indicating a region of one of the body templates, map the input to the body surface coordinate system, regenerate the body template to illustrate the indicated region on the template based on the body surface coordinate system with the mapped input, and display the regenerated body template via the display.

44. The device of claim 43, wherein the plurality of body templates comprises a front view template and a back view template.

45. The device of claim 43, wherein the plurality of body templates comprises a front view template, a right-side view template, a back view template, and a left-side view template.

46. The device of claim 43,
wherein the regenerated body template is a first one of the body templates that illustrates a portion of the surface, and
wherein the processor generates a second one of the body templates to illustrate at least some of the portion of the surface illustrated by the first one of the body templates and at least a portion of the region indicated by the user based on the body surface coordinate system with the mapped input, and displays the second one of the body templates via the display.

47. The device of claim 43, further comprising a user input circuit, wherein the processor receives commands from the user via the user input circuit, and sequentially displays the body templates via the display according to the commands.

48. The device of claim 47, wherein the display comprises the user input circuit, and the processor receives the commands from the user via the display.

49. The device of claim 47, wherein the processor displays at least one rotation direction arrow via the display for receiving the commands from the user.

50. The device of claim 43,
wherein the one of the body templates comprises a first one of the body templates, and
wherein the processor generates a second one of the body templates to illustrate a view of the external surface of the human body, the angle of rotation of the surface about the axis for the second one of the body templates based on a proximity of the received body region indication to an edge of the first one of the body templates, and displays the second one of the body templates via the display.

51. The device of claim 43, wherein the processor generates each of the body templates based on the body surface coordinate system.

52. The device of claim 43, wherein the body surface coordinate system comprises a three-dimensional coordinate system.

53. The device of claim 52, wherein the processor generates the three-dimensional coordinate system by applying one of a linear interpolation, a higher-order interpolation, or a spline technique to determine valid body coordinates.

54. The device of claim 43, wherein the body surface coordinate system comprises a two-dimensional coordinate system.

55. The device of claim 54, wherein the processor generates the two-dimensional coordinate system by mathematically peeling and flattening a representation of the external surface of the human body, and indicating continuity at edges of the body surface.

56. The device of claim 54, wherein the processor displays one of the body templates by projecting the two-dimensional coordinate system onto a three-dimensional frame representation of the external surface of the human body.

57. The device of claim 43, wherein the display comprises the user input circuit, and the processor receives the input via the display.

58. The device of claim 57, wherein the user interacts with the display using a stylus.

59. The device of claim 43, wherein the device comprises a programming device to program a neurostimulation therapy device that provides electrical stimulation to a patient.

60. The device of claim 43, wherein the device comprises a handheld computing device.

* * * * *